US005916869A

United States Patent [19]
Croom, Jr. et al.

[11] Patent Number: 5,916,869
[45] Date of Patent: Jun. 29, 1999

[54] METHOD OF TREATING BIRDS IN OVO

[75] Inventors: Warren J. Croom, Jr., Cary, N.C.; Ian L. Taylor, Kiawah Island, S.C.; Barbara A. Coles, Clayton, N.C.

[73] Assignees: North Carolina State University, Raleigh, N.C.; Medical University of South Carolina, Charleston, S.C.

[21] Appl. No.: 08/866,207

[22] Filed: Jun. 13, 1997

[51] Int. Cl.[6] .......................... A61K 38/00; A01N 37/18; C07K 2/00; C07K 16/00
[52] U.S. Cl. .................................. 514/2; 514/12; 514/13; 514/14; 514/17; 514/15; 514/16; 514/21; 530/324; 530/325; 530/300
[58] Field of Search ................................ 530/324, 325, 530/300; 514/12, 2, 13

[56] References Cited

U.S. PATENT DOCUMENTS

| | | |
|---|---|---|
| 4,647,567 | 3/1987 | Croom et al. . |
| 4,652,571 | 3/1987 | Croom et al. . |
| 4,701,441 | 10/1987 | Kalra . |
| 4,839,343 | 6/1989 | Waeber et al. ............................. 514/12 |
| 4,857,534 | 8/1989 | Croom et al. . |
| 5,328,899 | 7/1994 | Boublik et al. . |
| 5,516,653 | 5/1996 | Bard et al. . |
| 5,545,549 | 8/1996 | Gerald et al. . |
| 5,574,010 | 11/1996 | McFadden . |
| 5,602,024 | 2/1997 | Gerald et al. . |
| 5,604,203 | 2/1997 | Balasubramaniam . |
| 5,621,079 | 4/1997 | Cascieri et al. . |

FOREIGN PATENT DOCUMENTS

| | | | |
|---|---|---|---|
| WO93/24515 | 12/1993 | WIPO ............................. | C12P 21/00 |
| WO 96/22783 | 8/1996 | WIPO ............................. | A61K 38/00 |

OTHER PUBLICATIONS

Mantyh et al J. Neuroscience, 14/6:3958–3968, 1994.
Larhammar et al, JBC 267/16:10935–38, 1992.
Croom et al, J. Nutrition, 122/1:191–202, 1992.
Taylor et al, Biol. Bull. 177/2:187–191, 1989.
Hernandez et al, Am. J. Physiol, 266(Gastrointest. Liver Physiol. 29):G511–G516, 1994.
Raymond et al, FEBS Letters, 182/1:196–200, Mar., 1995.
Mangel et al, Regulatory Peptides 42:1–13, 1992.
Taylor, J. Dairy Sci, 76: 2094–2101, 1993.
Yoshinaga et al, Am.J.Physiology 263:G695–G701, 1992.
Adrian et al.; "Human Distribution and Release of a Putative New Gut Hormone, Peptide YY"; *Gastroenterology*, 89:1070–1077 (1985).
Adrian et al.; "Effect of Peptide YY on Gastric, Pancreatic, and Bilary Function in Humans"; *Gastroenterology*, 89:494–499 (1985).
Bird et al.; "Jejunal Guocose Absorption Is Enhanced by Epidermal Growth Gactor in Mice[1,2,3]"; *Nutrient Metabolism*, pp. 231–240 (1993).
Bird et al., "Peptide Regulation of Intestinal Glucose Absorption"; *J. Anim. Sci.*, 74:2523–2540 (1996).
Bilchik et al.; "Peptide YY Is a Physiological Regulator of Water and Electrolyte Absorption in the Canine Small Bowel In Vivo"; *Gastroenterology*, 105:1441–1448 (1993).
Croom, Jr. et al.; "Manipulation of Gastrointestinal Nutrient Delivery in Livestock[1,2]"; *J. Dairy Sci.*, 76:2112–2124 (1993).
Gaginella; "Absorption and secretion in the colon"; *Current Opinion in Gastroenterology*, 10:5–10 (1994).
Kalogeris et al.; "Control of Synthesis and Secretion of Intestinal Apolipoprotein A–IV by Lipid[1,2,3]"; *Amer. Soc. for Nutritional Sci.*, pp. 537S–543S (1997).
Obst et al.; "Ontogenesis of Intestinal Nutrient Transport in Domestic Chickens (Gallus Gallus) and It's Relation to Growth"; *The Auk*, 109(3):451–464 (1992).
Opleta–Madsen et al.; "Epidermal growth factor upregulates intestinal electrolyte and nutrient transport"; *Amer. Physiol. Soc.*, pp. G807–G814 (1991).
Pironi et al.; "Fat–Induced Ileal Brake in Humans: A Dose–Dependent Phenomenon Correlated to the Plasma Levels of Peptide YY"; *Gastroenterology*, 105:733–739 (1993).
Playford et al.; "Preliminary report: role of peptide YY in defence against diarrhoea"; *The Lancet*, 335:1555–1557 (1990).
Savage et al.; "Effects of peptide YY (PYY) on mouth to caecum intestinal transit time and on the rate of gastric emptying in healthy volunteers"; *Gut*, 28:166–170 (1987).
Servin et al.; "Peptide–YY and Neuropeptide–Y Inhibit Vasoactive Intestinal Peptide–Stimulated Adenosine 3',5'–Monophosphate Production in Rat Small Intestine: Structural Requirements of Peptides for Interacting with Peptide–YY–Preferring Receptors"; *Endocrinology*, 124(2):692–700 (1989).
Schwartz et al.; "Influence of Epidermal Growth Factor on Intestinal Function in The Rat: Comparison of Systemic Infusion Versus Luminal Perfusion"; *The Amer. J. of Surgery*, 155:18–23 (1988).
Yeo et al.; "Meal–stimulated absorption of water and electrolytes in canine jejunum"; *Amer. Physiol. Soc.*, pp. G402–G409 (1990).
Zhang et al.; "Characterization of Peptide–YY Release in Response to Intracolonic Infusion of Amino Acids"; *Endocriniology*, 132(2):553–557 (1993).
Abstract: "Intravenous Infusion of Peptide YY (PYY) Stimulates Jejunal Synthesis and Lymphatic Secretion of Apolipoprotein A–IV in Rats"; *Gastroenterology*, 110(4):A809 (1996).

*Primary Examiner*—Nita Minnifield
*Attorney, Agent, or Firm*—Myers Bigel Sibley & Sajovec, P.A.

[57] ABSTRACT

Methods are disclosed for administering Peptide YY (PYY) receptor agonists to birds in ovo to promote altricial development of the intestinal tract of neonatal birds. Enhanced altricial development of the small intestine in hatchling birds results in an increased absorption of nutrients from the small intestine without a concomitant increase in energy expenditure, thereby resulting in an improved efficiency of nutrient utilization, enhanced rate of post-hatch growth, and reduced post-hatch mortality rate in PYY-treated birds.

43 Claims, 3 Drawing Sheets

METHOD OF TREATING BIRDS IN OVO

FIELD OF THE INVENTION

This invention relates to methods of improving growth, feed efficiency, and survivability in hatchling birds. More specifically, the present invention relates to methods of treating birds in ovo so as to enhance nutrient absorption by the small intestine and the efficiency of nutrient utilization in the treated bird after hatch.

BACKGROUND OF THE INVENTION

Avian species have a unique organ development pattern compared to mammals. Birds expend a very high percentage of their initial energy supply on early development of the supply organs (those organs that supply nutrients and oxygen for survival), especially the digestive tract. Indeed on a per unit of body weight basis, neonatal domestic poultry have a larger gastrointestinal tract than most species. Lilja and Marks, *Growth, Development and Aging* 55, 219 (1991). Paradoxically, the functional development of the gastrointestinal tract (i.e. the ability to digest and absorb nutrients) occurs at a slower rate than gut growth in turkeys. Liu, *Comparison of sucrase, maltase and alkaline phosphatase activities in embryonic duodena between domestic and wild turkeys,* M. S. Thesis, North Carolina State University (1991). This is of great concern since in the modern broiler chick it has been shown that the ability to absorb glucose from the intestinal tract is barely able to meet demands necessary for growth. Obst and Diamond, *Auk.* 109, 451 (1992). This has been interpreted by Croom et al., *J. Dairy Sci.,* 71, 2112 (1993), to suggest that intestinal absorption may be limiting the phenotypic expression of the genetic potential of modern livestock and poultry. Fan found that selection for rapid growth in turkeys did not result in concomitant improvements in the rate or efficiency of glucose absorption from the jejunum, suggesting that the nutrient absorption by the gut is rate-limiting for growth. Fan, Ph.D. Dissertation, *Effect of Genetic Selection on Energetic Efficiency of Small Intestinal Glucose Absorption,* Department of Animal Science, North Carolina State University (1994). Similar findings have been reported for high egg production chickens by Majumdar and Panda, *Indian J. Anim. Sci.* 64, 1165 (1994).

Recent studies at North Carolina State University have demonstrated that the development of intestinal function in the hatchling of the modern domestic turkey is delayed relative to their wild ancestors. Coles et al., *FASEB J.* 7, A588 (1993). Other findings suggest that genetic selection for growth, feed efficiency and muscling may have resulted in unforseen decreases in the ability of the young poult to digest and absorb feedstuffs. Failure to assimilate and absorb vital nutrients at a young age, when systems important to survival (immune and digestive) are at a critical stage of development, may place a weakened hatchling at a higher risk for early death from disease.

In particular, mortality of neonate turkeys is greater than in most other poultry species. Mortality of unknown etiology accounts for nearly 50% of all management-related deaths in the U.S. turkey industry (Minnesota Statistical Reporting Service). On the average, 2 to 5% of all poults placed in brooder houses in the United States die of unknown causes before they begin to grow. The etiology of this occurrence is unknown. Poults dying without a known cause have been given the name of "starveouts" by some industry personnel because they appear weak and emaciated. In 1995, approximately 360 million turkeys were produced in the United States. If there is a 2% loss to unknown causes with an average market weight of 25 lbs with a value of $0.40 per pound, this loss costs turkey producers $72 million dollars a year.

An additional cause of hatchling mortality in the turkey industry has been the sudden and devastating appearance of the disease Poult Enteritis Mortality Syndrome (PEMS). The onset of this disease in young turkeys is characterized by severe flushing followed by very high death rates which peak at about two weeks of age. Barnes et al., *Poult Enteritis Mortality Syndrome (Spiking Mortality of Turkeys) and Related Disorders—Update,* Technical White Paper, Department of Poultry Science, North Carolina State University (1995). Those birds that do survive have severely depressed growth and are sometimes unsalvageable. The cause of this phenomenon is unknown. The increasing frequency of its occurrence is rapidly adding to the amount of monies loss by the industry to events associated with neonatal death.

Recently, Croom and colleagues have demonstrated that the exogenous administration of epidermal growth factor (EGF) and Peptide YY (PYY) increases glucose absorption in young growing mice. Bird et al., *J. Anim. Sci.,* 2523 (1996); Bird et al., *J. Nutr.* 124, 231 (1994). Both of these peptides are active orally. PYY has previously been shown to delay gastric emptying and intestinal transit time and to decrease pancreatic enzyme secretion. Savage et al., *Gut,* 28, 166 (1987); Pironi et al., *Gastroenterology* 105, 733 (1993); Adrian et al. *Gastroenterology* 89, 494 (1985). Of particular interest is the ability of PYY to increase glucose absorption without corresponding increases in the energetic cost of digestion. Bird et al., *J. Anim. Sci.,* 2523 (1996). This should result in an increase in net energy absorbed. This technology is currently the subject of co-pending U.S. patent application No. 08/379,354 to Croom et al. Other scientists have shown that both EGF and PYY increase intestinal absorption of amino acids (Schwartz and Storozuk, *Amer. J. Surg.* 155, 18 (1988)) and fat (Kalogeris et al., *Gastro.* 110, A809 (1996)).

Accordingly, the present invention addresses an unmet need for new technologies for preventing and/or attenuating the effects of various causes of neonatal mortality in birds. In particular, disclosed herein are methods of enhancing precocial development of the digestive tract of hatchlings prior to hatching so that the young bird is better able to benefit from high quality nutrition and management strategies resulting in healthier and thriftier birds.

SUMMARY OF THE INVENTION

Croom et al., *J. Dairy Sci.* 76, 2112 (1993), have previously suggested that absorption of glucose and other nutrients can be rate-limiting for growth and feed efficiency in domestic livestock and poultry. Altricial development of the small intestines of hatchling birds may exacerbate this problem and contribute to the high mortality rate of neonatal birds due to stunting and disease. Stunting is a non-specific decrease in growth of unknown etiology. It is postulated that stunting is due to an altricial development of the gastrointestinal tract. Disclosed herein are methods of enhancing precocial development of the hatchling small intestine by in ovo administration of PYY, thereby improving nutrient absorption, the efficiency of nutrient utilization, and survivability in hatchlings.

As a first aspect, the present invention provides a method of enhancing the growth of a bird comprising administration of a Peptide YY (PYY) receptor agonist to a bird in ovo and then incubating the bird to hatch, wherein the PYY receptor agonist is administered in ovo in an amount effective to enhance the growth of the bird.

As a second aspect, the present invention provides a method of improving the efficiency of feed utilization in a bird comprising administration of a PYY receptor agonist to a bird in ovo, and then incubating the bird to hatch, wherein the PYY receptor agonist is administered in ovo in an amount effective to improve the efficiency of feed conversation of the bird after hatch.

As a third aspect, the present invention provides a method of reducing mortality in a bird comprising administration of a Peptide YY (PYY) receptor agonist to a bird in ovo; then incubating the bird to hatch, wherein the PYY receptor agonist is administered in an amount effective to reduce mortality of the bird after hatch.

As fourth aspect, the present invention provides a method of enhancing gastrointestinal absorption of a sodium-dependent co-transported nutrient in a bird, comprising administration of a PYY receptor agonist to a bird in ovo, then incubating the bird to hatch, wherein the PYY receptor agonist is administered in ovo in an amount effective to enhance the gastrointestinal absorption of the sodium-dependent co-transported nutrient after hatch.

These and other aspects of the present invention are set forth in more detail in the description of the invention below.

DETAILED DESCRIPTION OF THE INVENTION

The present inventors have previously found that exogenously administered Peptide YY (PYY) not only increases nutrient transport across the intestinal absorptive epithelial cell (enterocyte) luminal membrane, the transport is increased without a concomitant increase in energy expenditure by the intestinal tract, as described in co-pending U.S. patent application No. 08/379,354 to Croom et al. As disclosed herein, in ovo administration of PYY to birds results in increased nutrient transport across the small intestine, with a resulting increase in growth, improved efficiency of nutrient utilization, and decreased mortality in the bird after hatch.

In the intestine, transport of substances across the absorptive epithelial cell luminal membrane occurs by active transport and by passive transport. Active transport occurs against an electric or chemical gradient, requires the expenditure of energy, is carrier-mediated, and is subject to competitive inhibition. Passive transport occurs with the electric or chemical gradient, does not require energy and is not carrier-mediated. The absorption of both amino acids and sugars occurs by an active transport mechanism and requires the presence of sodium ions. See Hediger and Rhoads, *Physiological Reviews*, 74, 993 (1994). While there are reports in the literature that epidermal growth factor (EGF) increases the absorption of electrolytes and nutrients such as glucose and proline from the intestine (Opleta-Madsen et al., *Am. J. Physiol.* 260, G807 (1991)), it is also reported that the energetic cost of transporting each unit of nutrient is similar to that described for control animals (Bird et al., *J. Nutr.* 124, 231 (1994)).

The luminal active glucose transporter in the small intestine, S-GLT1, is a protein encoded by one gene of a family of genes that also encodes the sodium-dependent proline transporter and a sodium-dependent neutral amino acid transporter (also known as Transporter A). Hence, it is probable that agents that increase sodium-dependent intestinal glucose transport will also increase sodium-dependent amino acid transport. This was observed recently in sheep injected with recombinant bovine growth hormone, where sodium-dependent duodenal active transport of glucose increased by approximately 60% and transport of proline increased by approximately 30%. Bird et al., *J. Anim. Sci.* 76, 343 (1996).

Recent evidence suggests that PYY stimulates glucose transport across the small intestine. Mice treated with PYY exhibit an increase in active jejunal glucose transport without a corresponding increase in passive transport rates. Bird et al., *J. Anim. Sci.*, 2523 (1996). Specifically, PYY appears to upregulate the number of active glucose transporters in the brush border. Moreover, the increase in active jejunal glucose transport in mice with PYY treatment occurs without any increase in intestinal energy expenditure. Id.

As used herein, gastrointestinal absorption refers to caloric uptake (i.e., absorption from the gut rather than mere ingestion), and enhancing gastrointestinal absorption refers to increasing total caloric uptake over that which would otherwise occur without PYY treatment. As used herein, nutrients refer to both carbohydrates, such as glucose, and amino acids, such as proline. As used herein, an increase (or decrease) in active uptake of a nutrient due to treatment of a subject with a PYY receptor agonist or antagonist refers to increased (or decreased) nutrient uptake over that which would have occurred in the bird without PYY treatment. Similarly, an increase or decrease in water absorption, refers to an increase or decrease over that which would have occurred in the bird without PYY treatment.

As used herein growth and growth enhancement refer to increases in either, or both, weight and size (e.g., height, width, diameter, circumference, etc.) over that which would otherwise occur without PYY treatment. Growth can refer to an increase in the mass (e.g., weight or size) of the entire animal or of a particular tissue (e.g., muscle tissue in general or a specific muscle). Alternatively, growth can indicate a relative increase in the mass of one tissue in relation to another, in particular, an increase in muscle tissue relative to other tissues (e.g., adipose tissue).

As used herein, improving the efficiency of feed utilization refers to a reduction in the Feed Conversion Ratio (FCR) as compared with that which would otherwise occur without PYY treatment. In ovo treatment of birds with PYY improves the FCR for growth by increasing gastrointestinal nutrient absorption without a concomitant increase in intestinal energy expenditure, thereby increasing the growth efficiency of the neonatal bird.

As used herein, reducing mortality refers to decreasing the death rate in neonatal birds (before, during or after hatch) as compared with that which would otherwise occur in the absence of PYY. Mortality may be from any cause, in particular, stress, stunting, "starveouts", and disease (e.g., PEMS).

In preferred embodiments of the invention, in ovo administration of PYY enhances gastrointestinal absorption, improves the efficiency of feed utilization, enhances growth, or reduces mortality in birds one week after hatch. Alternatively, in other preferred embodiments, in ovo administration of PYY enhances gastrointestinal absorption, improves the efficiency of feed utilization, enhances growth, or reduces mortality in birds at two, three, four, six, eight and fifteen weeks after hatch. In yet other preferred embodiments of the invention, in ovo administration of PYY to a bird increases hatchability (i.e., the percentage of birds that hatch and survive).

A. Uses of PYY in Methods of the Present Invention

The present invention may be carried out in any avian species, including, but not limited to chickens, turkeys, ducks, geese, quail, and pheasant, preferably chickens and turkeys. The PYY peptide and PYY agonists used in the methods of the present invention increase feed utilization efficiency in birds by increasing nutrient uptake by the hatchling bird without a concomitant increase in intestinal energy expenditure, thereby increasing the efficiency of post-hatch growth.

Recent studies indicate that in strains of domestic livestock highly selected for their rapid growth, the intestine's ability to absorb nutrients may be a growth limiting factor. In other words, the intestine functions at or near its assimilation limit so that increasing nutrient ingestion will not result in an increase in nutrient assimilation, and will not therefor contribute to increased growth. Croom et al., *J. Dairy Science* 76, 2112 (1993). Recent work by Obst and Diamond indicate that in strains of domestic chickens, the intestinal capacity to absorb nutrients imposes limits on normal growth. Obst and Diamond, *Auk* 109, 451 (1992). Thus, methods of the present invention may be used in normal (healthy) domestic poultry to increase feed utilization efficiency, and thus increase growth above that which could be achieved by any increase in feed intake alone.

One of the current issues regarding chick quality in the broiler industry is the question of precocial development of the hatchling digestive tract. Current dogma suggests that intensive genetic selection for increased growth has resulted in more altricial digestive tracts at birth. This failure of the intestinal tract of hatchling chicks to fully digest and absorb feed may contribute to increased post-hatch mortality and subsequent decreases in performance. Bird et al., *J. Anim. Sci.,* 2523 (1996) have reported that treatment of mice with exogenous PYY increased active jejunal glucose transport without a corresponding increase energy expenditure. The methods of the present invention may be practiced to promote precocial development of the small intestine of the neonatal bird, resulting in increased nutrient absorption by the gut, increased growth, and improved FCR after hatch. In this manner, the present invention provides methods for improving the nutritional status of the hatchling bird, and thereby increasing disease resistance and survivability after hatch.

PYY receptor antagonists may be used where a reduction in the uptake of nutrients, and in particular the uptake of glucose, is desired. Additionally, PYY receptor agonists may be used to treat flushing in neonatal birds (i.e., diarrhea).

The PYY peptide, its receptor agonists and antagonists may also be used to screen substances for PYY receptor ligand activity, as binding to the receptor is subject to competitive inhibition. Methods of screening substances, such as by competitive binding assays, are known in the art and would be apparent to one skilled in the art.

B. Description of PYY

PYY (Peptide tyrosine tyrosine) is a 36 amino acid peptide hormone produced by "L type" endocrine cells. See Boucher et al., *Regul. Pept.* 13, 283 (1986). PYY is a member of the pancreatic polypeptide family, which includes pancreatic polypeptide (PP) and neuropeptide Y (NPY), in addition to Peptide YY. PPY is released in response to feeding and has a variety of effects on the gastrointestinal tract, including inhibition of gastric acid secretion, inhibition of pancreatic exocrine secretion, delay of gastric emptying, and slowing of intestinal transit. See Savage et al., *Gut* 28, 166 (1987); Pironi et al., *Gastroenterology* 105, 733 (1993); Adrian et al., *Gastroenterology* 89, 494 (1985).

Two forms of PYY, PYY (1-36) and PYY (3-36), have been identified in rabbits (Grandt et al., *Peptides* 15, 815 (1994)), dogs and humans (Grandt et al., *Regul. Pept.* 51, 151 (1994)). PYY (1-36) has been named PYY-I and PYY (3-36), PYY-II. As used herein, the term "PYY" indicates both PYY-I and PYY-II. Those skilled in the art will appreciate that PYY encompasses other PYY variants having substantial sequence similarity to PYY-I or PYY-II, which bind to PYY receptors so as to produce the physiological effects associated with PYY-I and PYY-II. Furthermore, PYY for use in the methods of the present invention may be from any species of origin, preferably from mammalian or avian species, and may be from natural sources or produced by genetic engineering techniques as is known to those skilled in the art.

Binding studies using labelled PYY have demonstrated the presence of a PYY receptor in rat small intestine. Servin et al., *Endocrinology* 124, 692 (1989), used fragments of PYY peptide to study the structural requirements of peptides for competing with labelled PYY for binding to intestinal membranes, and reported that fragments of PYY acted as agonists of intact PYY, although at reduced biological activity.

Thus far, seven potential receptor subtypes have been identified for the NPY-PYY peptide family. See, e.g., Larhammar, *Regulatory Peptides* 65, 165 (1996). Two receptors termed "Y1" and "Y2" are the best characterized; both of these receptors bind NPY as well as PYY. According to the methods of the present invention, PYY or its agonists/antagonists may act through any PYY receptor that binds PYY and transduces a cellular response to PYY binding.

In addition to the PYY peptide, PYY receptor agonists and antagonists may also be used in the methods of the present invention. As used herein "PYY agonist" means a substance which binds to the PYY receptor and induces the same physiologic responses as PYY. As used herein, "PYY antagonist" means a substance which binds to the PYY receptor and blocks the physiologic effect of PYY.

Methods of identifying receptor agonists and antagonists are well-known to those skilled in the art. PYY agonists and antagonists will typically bind to PYY receptors. Agonists will activate the PYY receptor. Activation can be assessed by changes to the receptor itself (e.g., conformational change, phosphorylation, internalization, etc.) or by induction of a physiological response, such as increased glucose absorption across the intestine without a concomitant increase in intestinal energy expenditure. Likewise, PYY receptor antagonists will block activation of the PYY receptor by PYY or other PYY receptor agonists.

C. Analogs

Analogs of the PYY peptide are an aspect of the present invention. As used herein, an "analog" is a chemical compound similar in structure to a first compound, and having either a similar or opposite physiologic action as the first compound. With particular reference to the present invention, PYY peptide analogs are those compounds which, while not having the amino acid sequences of the PYY peptide, are capable of binding to the PYY receptor. Such analogs may be peptide or non-peptide analogs, including nucleic acid analogs, as described in further detail below.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the PYY peptide may be designed and synthesized in accordance with known techniques. International PCT Application WO 93/24515 (Cornell Research Foundation, Inc.) reports the cloning and identification of a human NPY/PYY receptor.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science* 247, 28029 (1990); Rossmann, *Nature* 333, 392 (1988); Weis et al., *Nature* 333, 426 (1988); James et al., *Science* 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/ hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or lie; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules able to bind to the PYY receptor. See, e.g., Knight, *BIO/Technology* 8, 105 (1990); Itzstein et al, *Nature* 363, 418 (1993) (peptidomimetic inhibitors of influenza virus enzyme, sialidase). Itzstein et al., *Nature* 363, 418 (1993), modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al., *Science* 263, 380 (1994) regarding the rational design of bioavailable nonpeptide cyclic ureas that function as HIV protease inhibitors. Lam et al. used information from x-ray crystal structure studies of HIV protease inhibitor complexes to design nonpeptide inhibitors.

Analogs may also be developed by generating a library of molecules, selecting for those molecules which act as ligands for a specified target, and identifying and amplifying the selected ligands. See, e.g., Kohl et al., *Science* 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, Feb. 7, 1994) and nonpeptide polymers (see, e.g., "peptoids" of Simon et al., *Proc. Natl. Acad. Sci. USA* 89, 9367 (1992)). See also U.S. Pat. No. 5,270,170 to Schatz; Scott and Smith, *Science* 249, 386–390 (1990); Devlin et al., *Science* 249, 404406 (1990); Edgington, *BIO/Technology* 11, 285 (1993). Peptide libraries may be synthesized on solid supports, or expressed on the surface of bacteriophage viruses (phage display libraries). Known screening methods may be used by those skilled in the art to screen combinatorial libraries to identify PYY receptor ligands. Techniques are known in the art for screening synthesized molecules to select those with the desired activity, and for labelling the members of the library so that selected active molecules may be identified. See, e.g., Brenner and Lerner, *Proc. Natl. Acad. Sci. USA* 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., *Proc. Natl. Acad. Sci. USA* 89, 9367 (1992) (generation and screening of "peptoids", oligomeric N-substituted glycines, to identify ligands for biological receptors); U.S. Pat. No. 5,283,173 to Fields et al., (use of genetically altered Saccharomyces cerevisiae to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology* 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Nati. Acad. Sci. USA* 89, 8864 (1992) and Tsai and Keene, *J. Immunology* 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

D. Peptides, Agonists and Antagonists

The term PYY peptide agonist as used herein refers to molecules that bind to PYY receptors and result in the increased uptake of glucose without a concomitant increase in intestinal energy expenditure. PYY agonists may be fusion proteins containing the PYY peptide sequence or may be formed by modifying the PYY peptide's natural amino acid sequence or modifying the N-terminal amino and/or the C-terminal carboxyl group, and include salts formed with acids and/or bases, particularly physiologically acceptable inorganic and organic acids and bases. Additionally, PYY agonists may be truncated PYY peptides. Such peptides are known in the art and include PYY-(3-36), PYY-(4-36), PYY-(6-36), PYY-(10-36), PYY-(13-36), PYY-(24-36), and PYY-(27-36). See, e.g., Yoshinaga et al., *Amer. J. Physiol.* 263, G695 (1992). Preferred modifications are those which increase the affinity of binding to the PYY receptor, the activation of the PYY receptor, or distal PYY-induced responses. Also preferred are modifications which provide a more stable, active peptide which will be less prone to enzymatic degradation in vivo.

Peptides of the present invention may be made in accordance with techniques known in the art. Using accepted techniques of chemical synthesis, the peptide is built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide. Peptides of the present invention may also be produced through recombinant DNA procedures as are known in the art.

E. Administration of PYY, its Agonists or Antagonists

The term "in ovo," as used herein, refers to birds contained within an egg prior to hatch. Thus, the present invention may be conceived of as both a method of treating eggs and a method of treating birds. The present invention may be carried out on in any avian species, including, but not limited to chickens, turkeys, ducks, geese, quail, and pheasant, preferably chickens and turkeys.

In ovo administration of PYY, its agonists or antagonists may be at any time during incubation, the duration of which will vary depending upon the species. Preferably, the PYY, its agonists or antagonists are administered during the last quarter of in ovo incubation (e.g., days 16–21 of incubation in chicken eggs or days 21 to 28 in turkey eggs).

Dosage is not critical and will vary with the species being treated, the time, and site of administration, and the desired effect. The optimal dosage can be routinely determined by conventional methods. There is no particular upper limit to the dosage, but it may be as much as 150, 300, 600, 1,200, or 2,500 μg per kg of egg weight, or more. Likewise, there is no particular lower limit to the dosage, but it may be as little as 300, 150, 75, 10, 1, 0.5 or 0.1 μg per kg of egg weight, or less.

The term "in ovo administration," as used herein, refers to any means which transports the peptide through the shell. The preferred method of administration is, however, by injection. PYY, its agonists or antagonists may be introduced into any region of the egg that allows effective uptake by the embryonic bird, including the albumen, air cell, allantois, the yolk sac, the yolk, the chorio-allantoic membrane, the amnion, or the embryo itself, with the air cell, amnion, or embryo being preferred. In general, it is preferable to inject into the amnion or embryo when the egg is a chicken egg and into the air cell when the egg is a turkey egg. A key consideration when injecting PYY, its agonists or antagonists into the air cell or amnion is that the injection must be made before pipping or rupture of the air cell by the embryo, because this event will disrupt the link between the embryonic bird circulation and the membrane.

Any suitable means may be used for introducing PYY, its agonists or antagonists in ovo, including in ovo injection, high pressure spray through the egg shell, and ballistic bombardment of the egg with microparticles carrying the PYY, its agonists or antagonists thereto.

The mechanism of injection is not critical, but it is preferred that the method not unduly damage the tissues and organs of the embryo or the extraembryonic membranes surrounding it so that the treatment will not decrease hatch rate. A hypodermic syringe fitted with a needle of about 18–26 gauge is suitable for the purpose. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being the EMBREX INOVOJECT™ system (described in U.S. Pat. No. 4,681,063 to Hebrank) and devices disclosed in U.S. Pat. Nos. 4,040,388, 4,469047, and 4,593,646 to Miller. All such devices, as adapted for practicing the present invention, comprise an injector containing PYY, its agonists or antagonists, as described herein, with the injector positioned to inject an egg carried by the apparatus with the PYY, its agonists or antagonists. In addition, if desired, a sealing apparatus operatively associated with the injection apparatus may be provided for sealing the hole in the egg after injection thereof.

Preferred apparatus for practicing the present invention is disclosed in U.S. Pat. No. 4,681,063 to Hebrank and U.S. Pat. No. 4,903,625 to Hebrank. This device comprises an injection apparatus for delivering fluid substances into a plurality of eggs and suction apparatus which simultaneously engages and lifts a plurality of individual eggs from their upwardly facing portions and cooperates with the injection means for injecting the eggs while the eggs are engaged by the suction apparatus. The features of this apparatus may be combined with the features of the apparatus described above for practicing the present invention. Those skilled in the art will appreciate that this device can be adapted for injection into any portion of the egg by adjusting the penetration depth of the injector.

F. Medicaments

In the manufacture of a medicament according to the present invention, hereinafter referred to as a pharmaceutical formulation, the active compound (PYY, PYY agonist or PYY antagonist, or analogs thereof) is typically admixed with a pharmaceutically acceptable carrier. For injection into eggs, the carrier will typically be a liquid. For other methods of administration, the carrier may be either solid or liquid, such as sterile, pyrogen-free water or sterile pyrogen-free phosphate-buffered saline solution. One or more active compounds may be incorporated in the formulations of the invention, which may be prepared by any of the well known techniques of pharmacy.

In some embodiments of the invention, the bird is treated with the active compound, as described above, both in ovo and after hatch. In formulations of the active compounds of the present invention for administration to birds post-hatch, the active compound is included in an amount effective to accomplish the intended treatment. In general, PYY and its agonists are included in an effective nutrient transport stimulating amount; PYY antagonists are included in an effective nutrient transport inhibiting amount. Alternately, the PYY receptor agonist is included in an amount effective to enhance growth, improve the efficiency of feed utilization, or reduce mortality in a bird after hatch.

The precise amount to be administered to the bird after hatch is determined in a routine manner, and will vary depending on the age and species of bird, the desired effect, and the route of administration. In general, for PYY the dosage administered will be sufficient to result in peak plasma PYY concentrations of from about $1 \times 10^{-1}$, $1 \times 10^{0}$ or $1 \times 10^{1}$ picomole per Liter to about $1 \times 10^{2}$, $1 \times 10^{3}$ or even $1 \times 10^{4}$ picomole per Liter or more. Preferred dosages may be determined by simply administering a composition containing a known amount of active ingredient to a bird, and monitoring the bird for the desired effect, as would be known by one skilled in the art.

For the preparation of these compositions for administration to a bird after hatch, use can be made of pharmaceutical carriers adapted for conventional forms of administration, for example, injection solutions, tablets, capsules, dragees, syrups, solutions, suspension and the like. As an injection medium, it is preferred to use water which contains the additives usual in the case of injection solutions, such as stabilizing agents, salts or saline, and/or buffers. The active agent or its pharmaceutical formulation may be contained within a nutritional medium, e.g., in nutritional supplements. Oral formulations may be slow release preparations or enteric coated preparations to facilitate delivery of the peptide to the small intestine.

When administering PYY, its agonists and antagonists to a bird post-hatch, any suitable route of administration may be employed, including administration by parenteral injection (e.g., subcutaneous, intramuscular, or intradermal), or by oral or topical administration.

The following examples are provided to illustrate the present invention, and should not be construed as limiting thereof. In these examples, g means gram, mg means milligram, μg means microgram, mm means millimeter, μmol means micromole, mmol means millimole, pmole means picomole, L means liter, mL means milliliter, μL means microLiter, MBq means megabecquerel, kBq means kilobecquerel, 3OMG means tritiated 3-O-methyl-D-glucose, and phlorizin means phloretin-2'-β-D-glucoside.

EXAMPLE 1

In ovo Administration of PYY to Broiler Chicks

We hypothesized that in ovo administration of PYY would result in more precocial development of the small intestines of broiler chicks, thereby increasing gut absorption of dietary nutrients, especially glucose, by young birds.

To test this hypothesis, the following study was carried out: Four hundred and sixty eggs were randomly divided into two groups and administered either saline (control) or PYY (600 μg/kg egg weight) into the air cell on day 18 of incubation. At hatching 420 chicks were vent sexed, wing-banded, weighed and randomly placed by treatment and sex into 60 pens of 7 chicks each. Pens were equipped with chick founts, nipple drinkers, and feeders. Bird rooms were maintained at 86–90° F. for the first week and the temperature gradually decreased to 65–68° F. at week six. The light cycle was 23 light and 1 dark for the entire experiment.

Chicks were fed a starter diet (22% CP) for the first 3 weeks and a grower diet (20% CP) for the remaining 3 weeks. Individual chicks were weighed weekly and pen feed consumption recorded as feeders were refilled. At week six, all birds were weighed and euthanized with $CO_2$. Data were statistically analyzed using the General Linear Models Procedure of SAS (1988) with treatment, sex, room and pen as the main effects. Differences were considered significant at $P<0.05$.

EXAMPLE 2

In ovo Administration of PYY Improves Growth and FCR of Broiler Chicks

Weight gain and Feed Conversion Ratio (FCR) were evaluated in broiler chicks treated in ovo with PYY as described in Example 1. Although there were sex differences ($P<0.05$) for many of the growth and performance parameters, there were no sex x treatment interactions ($P<0.05$). Therefore, data from both sexes was combined. Mortality was less than 1% for all birds and did not differ significantly between treatments.

Figure 1:
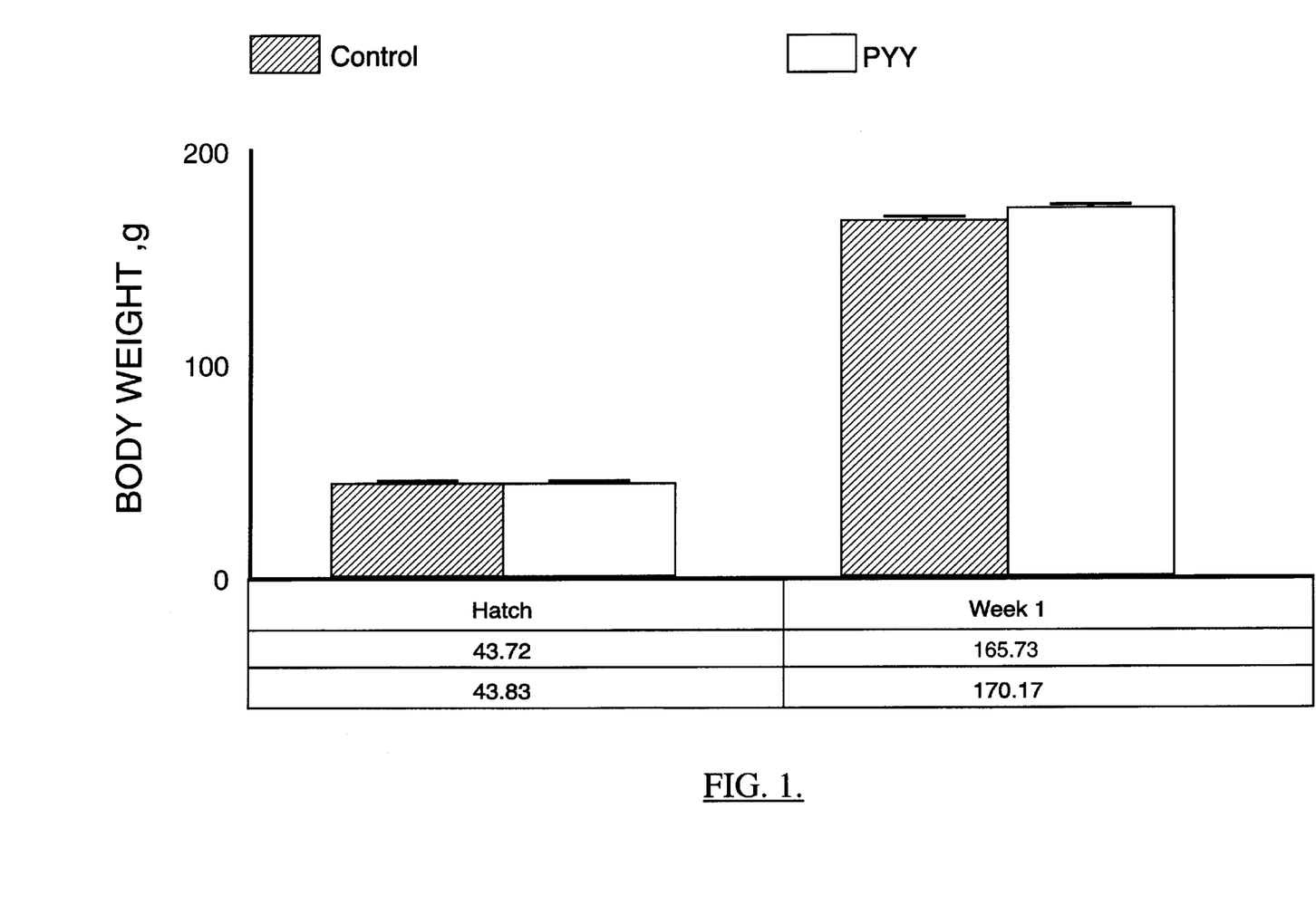
FIG. 1 shows the effects of in ovo injections of saline (control) and PYY on broiler chick weights at hatch and week 1 of age. Body weights of chicks from PYY treated eggs were significantly ($P<0.05$) greater.
Figure 2:
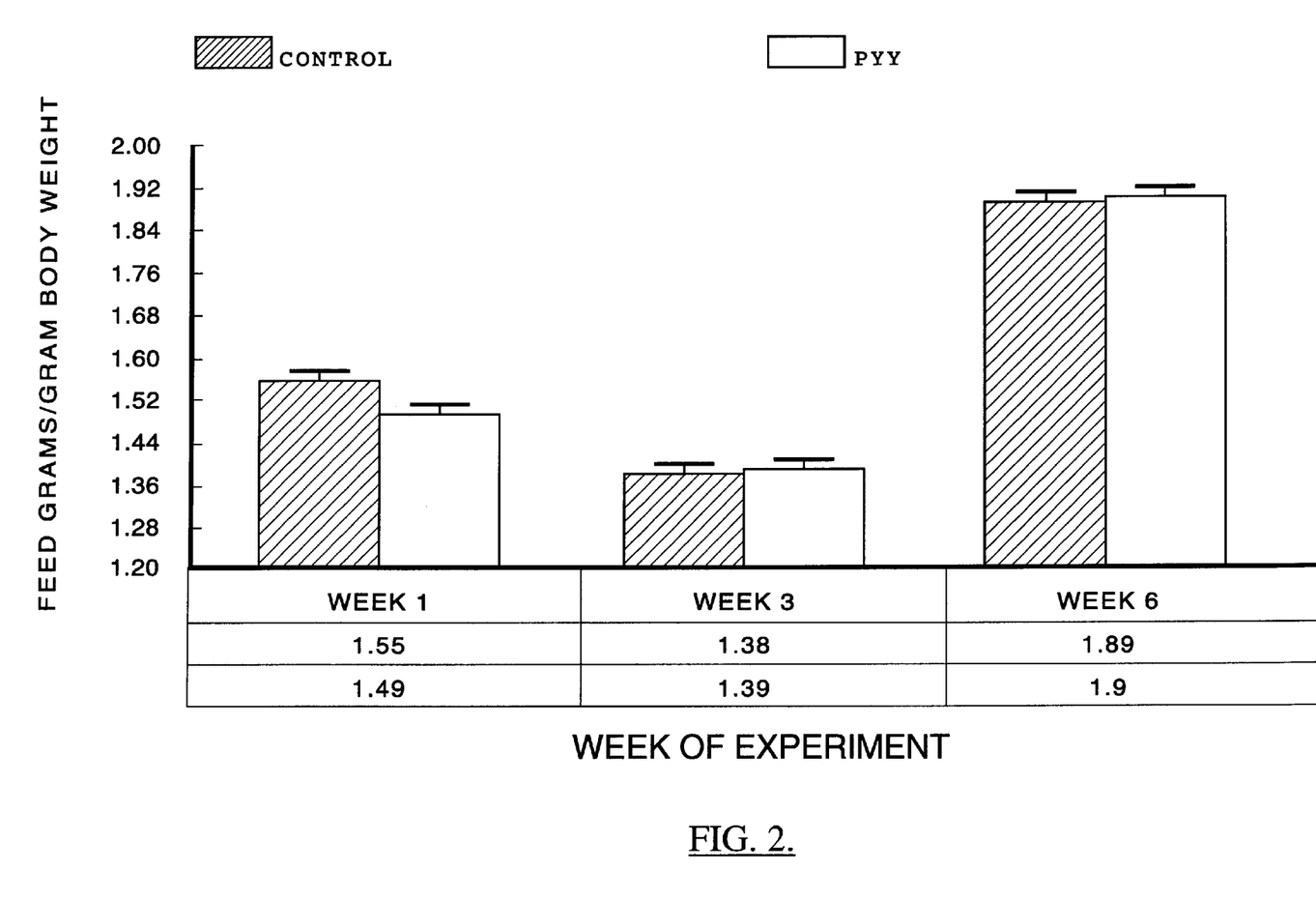
FIG. 2 presents the effects of in ovo injections of saline (control) and PYY on broiler chick FCR at weeks 1, 3 and 6. FCR of birds from PYY treated birds at week 1 were significantly lower ($P<0.05$).

FIG. 1 depicts broiler chick body weights at hatch and at weeks 1, 3 and 6. Chicks from PYY treated eggs were 2.7% heavier ($P<0.22$) at week 1 than chicks from control eggs. No statistical differences were noted in broiler weights at weeks 3 and 6 (data not shown). Similarly, the FCR was 3.99% less in chicks from PYY treated eggs at one week of age as compared with chicks from saline treated eggs (FIG. 2). No differences were noted in FCR at weeks 3 and 6 (data not shown).

Chicks from eggs treated in ovo with PYY were heavier and had better FCR than broiler chicks from eggs treated in ovo with saline. These data suggest that absorption of glucose and other nutrients can be rate-limiting for growth and feed efficiency in domestic livestock and poultry as proposed by Croom et al. (J. Dairy Sci., 76:2112, 1993). Moreover, in ovo administration of PYY improves both chick growth and feed efficiency, suggesting that PYY enhances precocial development of the small intestine in hatchling chicks, thereby improving net absorption of nutrients and efficiency of nutrient utilization.

EXAMPLE 3

Treatment with PYY Post-Hatch

It is likely that the increase in performance observed in Example 2 did not persist after week 1 post-hatch is due to sloughing of enterocytes whose transport processes were upregulated by PYY in ovo. This performance increase would probably be maintained throughout the growing cycle if PYY were re-administered to the birds post-hatch.

Chicks are treated in ovo with PYY as described in Example 1. Weight and FCR are measured as described in Example 2. Hatchling birds are treated again with a biologically-effective dose of PYY at one or more times post-hatch. The dose of PYY to be administered and treatment times are chosen so as to maximize precocial development of the hatchling gut. Precocial development of the small intestine can be evaluated by increased nutrient absorption, enhanced post-hatch growth, improved FCR, and reduced hatchling mortality. The development of the small intestine can also be assessed by histomorphological analysis.

EXAMPLE 4

In ovo Treatment of Turkey Poults with PYY and EGF

Thirty turkey eggs were randomly divided into three groups and administered 0.25 ml of a solution containing either saline (control), EGF (600 μg/kg egg weight) or PYY (600 μg/kg egg weight) into the air cell on day 25 of incubation. The solutions were administered to each egg through a small hole made in the egg shell directly above the air sec, the solutions were injected directly on top of the air cell membrane. On day 28 of incubation, the birds were killed and body weight was measured. After sacrifice, the small intestine was removed from each bird, and the weight and length were measured.

EXAMPLE 5

Effect of in ovo Administration of PYY or EGF on Jejunal Glucose Transport

A sample of mid-jejunal tissue was dissected out of each of the small intestines removed in Example 4. Each glucose transport assay, as described below, was replicated three times per poult, and an assay to measure non-specific binding was replicated twice per poult. Thus each mid-jejunal sample (one from each poult) was cut into eight one millimeter rings.

The assay for glucose transport was a modification of the assay validated by Black, *Comp. Biochem Physiol.* 90A, 379 (1988), to measure glucose transport in embryonic chick duodenum. Additional details of the present method are discussed in Bird et al., *J. Nutr.* 124, 231 (1994), and Bird et al., *Nutr. Research*, 14, 411 (1974). The transport buffer utilized for jejunal samples was similar to that described by Black, but also contained 0.5 mmol/L 3-O-methyl-D-glucose (3OMG), 0.5 mmol/L B-hydroxybutyrate, and 2.5 mmol/L glutamine. The assay was started by transferring intestinal rings preincubated at 37° C. for 5 minutes in transport buffer to beakers containing 28 MBq/L of [$^3$H] 3OMG in 2 ml of buffer. To differentiate active from passive transport, phlorizin (phloretin-2'-β-D-glucoside; Sigma Chemicals, St. Louis, Mo.) was utilized. Phlorizin is a specific inhibitor of the S-GLT1 transporter (a sodium-dependent active transporter) located on the luminal surface of absorptive epithelium (see Brot-Laroche and Alvarado, *Mechanisms of sugar transport across the intestinal brush border membrane, in* INTESTINAL TRANSPORT: FUNDAMENTAL AND COMPARATIVE ASPECTS (Gilles-Baillin and Gilles eds., 1983)). The S-GLT1 transporter is one of a family of transporter proteins, and actively transports glucose. 3OMG is transported by S-GLT1, but is not metabolized by the epithelial cell and hence accumulates in the cell (see Kimmich and Randalls, *J. Membrane Biol.* 23, 57 (1975). Phlorizin was added at 1 mmol/L to the buffer in an additional set of incubations. A 5 minute concomitant incubation of duplicate samples at 4° C. measured nonspecific binding of [$^3$H]3OMG. Thus each mid-jejunal sample was cut into eight one millimeter rings; three rings were assayed in the absence of phlorizin at 37° C., three rings were assayed in the presence of phlorizin at 37° C., and two rings were assayed in the presence of phlorizin at 4° C. to measure background nonspecific binding of [$^3$H]3OMG.

Uptake of [$^3$H]3OMG was stopped after 5 minutes by rinsing samples in 3 ml of ice-cold mannitol (300 mmol/L). Labelled substrate was extracted from the tissue into 2 mL of trichloroacetic acid (25 g/L) at 37° C. for 60 minutes in a shaking water bath. Samples were removed, blotted and weighed. The extract was centrifuged at 2000×g for 15 minutes at 4° C., and then 1 ml of the decanted supernatant was dispersed in 5 ml of Ecolite (+) scintillation cocktail (ICN Biomedicals, Cleveland, Ohio) and counted for 10 minutes in a scintillation counter. Duplicate aliquots (100 uL) of incubation media containing approximately 2.8 kBq [$^3$H]3OMG (both with and without phlorizin) and a blank were counted with each set of samples.

Active glucose transport was calculated as the difference between 3OMG accumulation in media with and without phlorizin. Passive transport was calculated as the difference between 3OMG accumulation in the presence of phlorizin at 37° C. and 4° C. Total transport is the difference between 3OMG accumulation at 37° C., in the absence of phlorizin, and accumulation at 4° C. in the presence of phlorizin. Transport data are presented as pmol glucose/(min-mg wet tissue).

Figure 3:
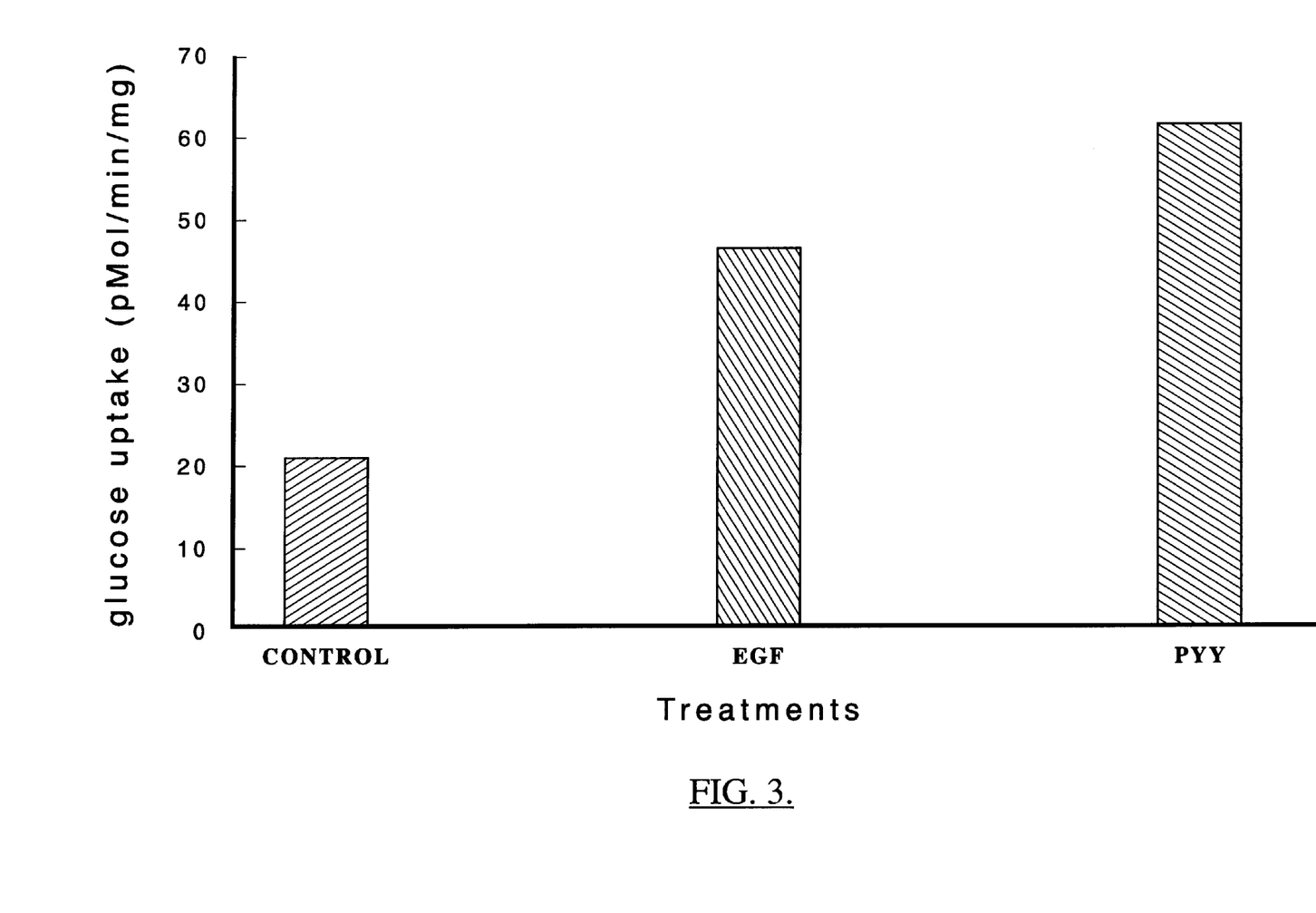
FIG. 3 presents the effects of in ovo administration of EGF and PYY on jejunal glucose transport in hatched turkey poults. Treatment with EGF or PYY increased glucose absorption at hatching from 200% to 300% ($p<0.03$).

As shown in FIG. 3, in ovo administration of EGF or PYY (600 μg/kg egg weight) at day 25 of incubation increases glucose absorption at hatching from 200 to 300%. Although the number of eggs treated was small (10 per treatment) the effect was dramatic and statistically significant (p<0.03). This approach will prove useful in inducing precocious development of absorptive mechanisms in commercial operations.

EXAMPLE 6

PYY Dose-Response Study

The optimal dose of PYY to be administered in ovo to turkeys for post-hatch growth and FCR is evaluated by measuring these parameters, as described in Example 1, following treatment of turkey poults in ovo over a range of PYY concentrations.

Seventy randomly selected turkey eggs are weighed and set. The eggs are randomly assigned to one of seven treatments in a 3×3 complete block design. The treatments are in ovo administration of either EGF or PYY at day 25 of incubation. Each peptide is administered at 150, 300 or 600 micrograms per kg of egg weight. On day 28 of incubation, the birds are killed and body weight, intestinal weight, intestinal length, yolk sac weight, jejunal mucosal alkaline phosphatase, and maltase, as well as jejunal glucose and jejunal oxygen consumption are measured. Additionally, jejunal segments are fixed and stained prior to histomorphometric analyses. All of these procedures have been previously used and have been described in the literature by Bird et al. (1994), Coles et al. (1993), and Fan et al. (1994). Egg weight will be used as a covariant in the analysis of data.

EXAMPLE 7

Efficacy Study

This study is designed to evaluate whether increasing glucose absorption in the small intestine of hatchling poults by in ovo administration of PYY results in enhanced survivability and performance. Furthermore, it will identify the length of time post-hatch of any benefits resulting from the in ovo treatment of the eggs.

Ninety turkey eggs are assigned to one of three treatments (30 birds per treatment) in a completely randomized design. All eggs are injected in ovo on day 25 with one of the following treatments; a. saline, b. EGF, c. PYY. The amount of EGF and PYY used will be based on those dosages identified as causing the most jejunal glucose transport in hatched poults in Example 6. All poults are weighed at hatching. Ten birds per treatment are killed on day 1, week 5 and week 15 and the same measurements described in Example 6 will be made. Additionally, feed intake estimates and weights of all turkeys are made weekly until time of killing. Hatching weights are used as a covariant in the analysis of data.

The foregoing examples are illustrative of the present invention, and are not to be construed as limiting thereof. The invention is defined by the following claims, with equivalents of the claims to be included therein.

That which is claimed is:

1. A method of enhancing the growth of a bird comprising:
   (a) administering a Peptide YY (PYY) receptor agonist to a bird in ovo; and then
   (b) incubating said bird to hatch,
wherein said PYY receptor agonist is administered in ovo in an amount effective to enhance the growth of said bird.

2. The method according to claim 1 wherein said bird is grown for at least one week after hatch.

3. The method according to claim 1 wherein said growth is an increase in weight.

4. The method according to claim 1 wherein said growth is an increase in muscle mass.

5. The method according to claim 1 wherein said PYY receptor agonist is administered to said bird during the last quarter of in ovo incubation.

6. The method according to claim 1 wherein said PYY receptor agonist is administered in an amount of from about 150 to 1200 μg/kg egg weight.

7. The method according to claim 1 wherein said administration step is carried out by injecting said compound into a region selected from the group consisting of the amnion, embryo, air cell, allantois, and albumen of the egg.

8. The method according to claim 1 wherein said bird is selected from the group consisting of chickens, turkeys, ducks, geese, quail and pheasant.

9. The method according to claim 1 wherein said bird is a chicken.

10. The method according to claim 1 wherein said bird is a turkey.

11. A method of improving the efficiency of feed utilization in a bird comprising:
    (a) administering a Peptide YY (PYY) receptor agonist to a bird in ovo; and then
    (b) incubating said bird to hatch,
wherein said PYY receptor agonist is administered in ovo in an amount effective to improve the efficiency of feed conversation of said bird after hatch.

12. The method according to claim 11 wherein said bird is grown for at least one week after hatch.

13. The method according to claim 11 wherein said PYY receptor agonist is PYY.

14. The method according to claim 11 wherein said PYY receptor agonist is administered to said bird during the last quarter of in ovo incubation.

15. The method according to claim 11 wherein said administration step is carried out by injecting said compound into a region selected from the group consisting of the amnion, embryo, air cell, allantois, and albumen of the egg.

16. The method according to claim 11 wherein said PYY receptor agonist is PYY.

17. The method according to claim 11 wherein said PYY receptor agonist is administered to said bird during the last quarter of in ovo incubation.

18. A method of reducing mortality in a bird comprising:
    (a) administering a Peptide YY (PYY) receptor agonist to a bird in ovo; then
    (b) incubating said bird to hatch,
wherein said PYY receptor agonist is administered in ovo in an amount effective to reduce mortality of said bird after hatch.

19. The method according to claim 18, wherein mortality is caused by Poult Enteritis Mortality Syndrome or stunting.

20. The method according to claim 18 wherein said PYY receptor agonist is PYY.

21. The method according to claim 18 wherein said PYY receptor agonist is administered to said bird during the last quarter of in ovo incubation.

22. The method according to claim 18 wherein said administration step is carried out by injecting said compound into a region selected from the group consisting of the amnion, embryo, air cell, allantois, and albumen of the egg.

23. The method according to claim 18 wherein said bird is selected from the group consisting of chickens, turkeys, ducks, geese, quail and pheasant.

24. The method according to claim 18 wherein said bird is a chicken.

25. A method of enhancing gastrointestinal absorption of a sodium dependent co-transported nutrient in a bird, comprising:
    (a) administering a Peptide YY receptor agonist to said bird in ovo; then
    (b) incubating said bird to hatch,
wherein said PYY receptor agonist is administered in ovo in an amount effective to enhance the gastrointestinal absorption of said sodium dependent co-transported nutrient after hatch.

26. The method according to claim 25 wherein said PYY receptor agonist is PYY.

27. The method according to claim 25 wherein said sodium dependent co-transported nutrient is selected from the group consisting of glucose, amino acids, and proline.

28. The method according to claim 25 wherein said PYY receptor agonist is administered to said bird during the last quarter of in ovo incubation.

29. The method according to claim 25 wherein said PYY receptor agonist is administered in an amount of from about 150 to 1200 μg/kg egg weight.

30. The method according to claim 25 wherein said administration step is carried out by injecting said compound into a region selected from the group consisting of the amnion, embryo, air cell, allantois, and albumen of the egg.

31. The method according to claim 25 wherein said bird is selected from the group consisting of chickens, turkeys, ducks, geese, quail and pheasant.

32. The method according to claim 25 wherein said bird is a chicken.

33. The method according to claim 9, wherein said administration step is carried out by injecting said compound into a region selected from the amnion and the embryo.

34. The method according to claim 10, wherein said administration step is carried out by injecting said compound into the air cell.

35. The method according to claim 24, wherein said administration step is carried out by injecting said compound into a region selected from the amnion and the embryo.

36. A method of enhancing the growth of a bird comprising:
   (a) administering a Peptide YY (PYY) receptor agonist selected from the group consisting of PYY or a truncated PYY to a bird in ovo; and then
   (b) incubating said bird to hatch,
wherein said PYY receptor agonist is administered in ovo in an amount effective to enhance the growth of said bird.

37. The method according to claim 36 wherein said bird is grown for at least three weeks after hatch.

38. The method according to claim 36 wherein said bird is grown for at least six weeks after hatch.

39. The method according to claim 36, wherein said PYY receptor agonist is selected from the group consisting of PYY-(4-36), PYY-(6-36), PYY-(10-36), PYY-(13-36), PYY-(24-36), and PYY-(27-36).

40. The method according to claim 36, wherein said PYY is PYY-(1-36).

41. The method according to claim 36, wherein said PYY is PYY-(3-36).

42. The method according to claim 36 further comprising the step of administering a compound selected from the group consisting of Peptide YY (PYY) or a truncated PYY to said bird after hatch.

43. A method of enhancing the growth of a bird comprising:
   (a) administering Peptide YY (PYY) to a bird in ovo; and then (b) incubating said bird to hatch,
wherein said PYY is administered in ovo in an amount effective to enhance the growth of said bird.

* * * * *